(12) United States Patent
Flohr et al.

(10) Patent No.: US 8,447,009 B2
(45) Date of Patent: May 21, 2013

(54) METHOD AND COMPUTED TOMOGRAPHY SCANNER FOR CARRYING OUT AN ANGIOGRAPHIC EXAMINATION

(75) Inventors: Thomas Flohr, Uehlfeld (DE); Michael Grasruck, Erlangen (DE); Bernhard Schmidt, Fürth (DE); Martin Sedlmair, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 13/182,616

(22) Filed: Jul. 14, 2011

(65) Prior Publication Data
US 2012/0014500 A1    Jan. 19, 2012

(30) Foreign Application Priority Data

Jul. 15, 2010 (DE) .......................... 10 2010 027 227

(51) Int. Cl.
*A61B 6/00* (2006.01)
*G06K 9/00* (2006.01)

(52) U.S. Cl.
USPC ............................... 378/5; 378/98.9; 382/130

(58) Field of Classification Search
USPC ............................ 378/5, 98.9, 98.12; 382/130
See application file for complete search history.

(56) References Cited

U.S. PATENT DOCUMENTS

| | | | |
|---|---|---|---|
| 3,848,130 A * | 11/1974 | Macovski | 378/98.9 |
| 3,974,386 A * | 8/1976 | Mistretta et al. | 378/98.11 |
| 4,506,327 A * | 3/1985 | Tam | 378/5 |
| 4,686,692 A * | 8/1987 | DeMeester et al. | 378/4 |
| 5,150,394 A * | 9/1992 | Karellas | 378/62 |
| 5,465,284 A * | 11/1995 | Karellas | 378/62 |
| 6,435,714 B1 * | 8/2002 | Bruder | 378/196 |
| 6,487,267 B1 * | 11/2002 | Wolter | 378/4 |

(Continued)

FOREIGN PATENT DOCUMENTS

| | | |
|---|---|---|
| CN | 1517071 A | 8/2004 |
| CN | 1589741 | 3/2005 |

(Continued)

OTHER PUBLICATIONS

German Priority Document DE 102010027227.2, Not yet published.

*Primary Examiner* — Alexander H Taningco
(74) *Attorney, Agent, or Firm* — Harness, Dickey & Pierce

(57) ABSTRACT

A method and a computed tomography scanner are disclosed for carrying out an angiographic examination of a patient, wherein the utilized computed tomography scanner includes at least one recording system mounted on a gantry such that it can rotate about a z-axis. Projection data is acquired from at least one prescribed angular position of the gantry for at least two different energies of X-ray radiation. The projection data is subsequently combined to form a resulting projection image by evaluating the projection data corresponding to the respective angular position, in which projection image at least one substance, which should be displayed selectively, is imaged with a high image contrast compared to the respective individual projection data. This procedure extends the field of application of the computed tomography scanner to projection-based angiography examinations, which were previously restricted to C-arm systems. 3D image reconstruction methods and projection methods can be carried out on opposite sides and with great flexibility during an examination, without the need for an additional modality. By using a multispectral technique, it is possible to contrast agent. The projection data at dispense with recording a native projection data record without the different energies are moreover acquired with no or little time offset, and so a computationally expensive and error-prone registration of the data records can be dispensed with.

25 Claims, 2 Drawing Sheets

U.S. PATENT DOCUMENTS

| | | | |
|---|---|---|---|
| 7,031,425 B2 * | 4/2006 | Hsieh et al. | 378/5 |
| 7,711,083 B2 * | 5/2010 | Heigl et al. | 378/20 |
| 7,738,625 B2 * | 6/2010 | Nishide et al. | 378/19 |
| 7,778,381 B2 * | 8/2010 | Nishide et al. | 378/4 |
| 7,873,141 B2 * | 1/2011 | Imai et al. | 378/5 |
| 2004/0101090 A1 * | 5/2004 | Drummond et al. | 378/4 |
| 2004/0264626 A1 * | 12/2004 | Besson | 378/4 |
| 2005/0047541 A1 * | 3/2005 | Tsuyuki | 378/4 |
| 2007/0104309 A1 * | 5/2007 | Schonborn et al. | 378/4 |
| 2007/0189443 A1 | 8/2007 | Walter et al. | |
| 2008/0260092 A1 | 10/2008 | Imai et al. | |
| 2010/0135557 A1 | 6/2010 | Krauss et al. | |

FOREIGN PATENT DOCUMENTS

| | | |
|---|---|---|
| DE | 19927953 A1 | 1/2001 |
| DE | 102007053511 A1 | 5/2008 |
| DE | 102008012893 A1 | 10/2008 |
| DE | 102007024158 A1 | 11/2008 |
| DE | 102007027460 A1 | 12/2008 |
| DE | 102009004186 A1 | 1/2010 |

* cited by examiner

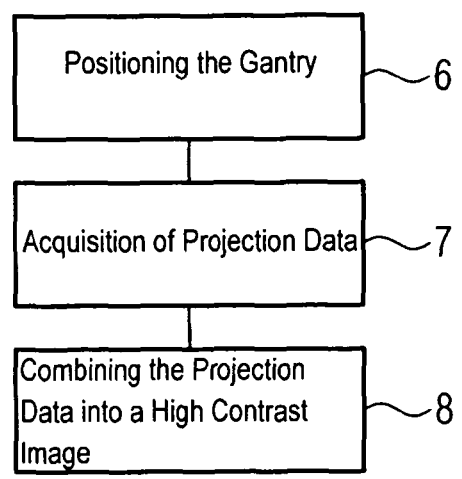
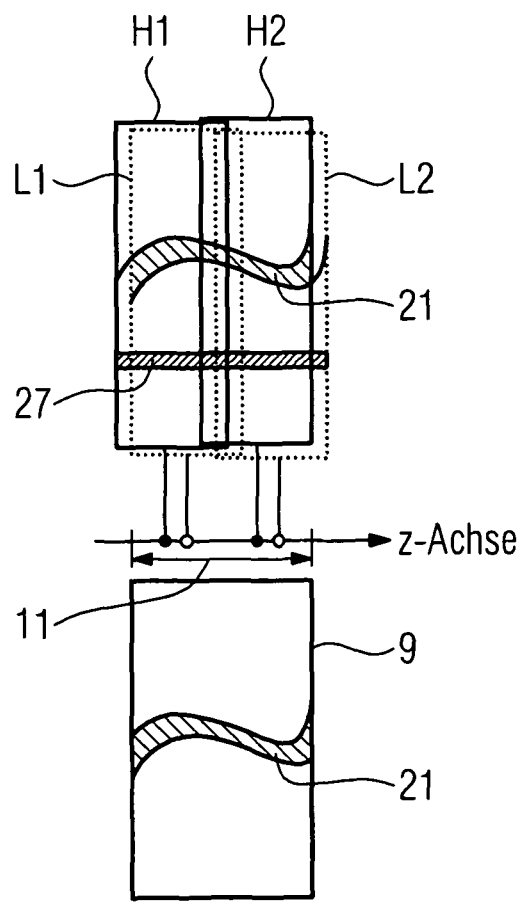

METHOD AND COMPUTED TOMOGRAPHY SCANNER FOR CARRYING OUT AN ANGIOGRAPHIC EXAMINATION

PRIORITY STATEMENT

The present application hereby claims priority under 35 U.S.C. §119 on German patent application number DE 10 2010 027 227.2 filed Jul. 15, 2010, the entire contents of which are hereby incorporated herein by reference.

FIELD

At least one embodiment of the invention generally relates to a method and/or a computed tomography scanner for carrying out an angiographic examination.

BACKGROUND

It is well-known that X-ray scanners are used in medicine to obtain information about the interior of a patient for the purpose of diagnosis and/or therapy. In the process, the different attenuation properties of the various substances with respect to X-ray radiation generated by the X-ray scanner are utilized for providing contrast in the image. Compared to soft tissue, bone tissue has very different attenuation properties. As a result of the high image contrast connected therewith, bone structures can be analyzed in a simple fashion. However, vessels and organs, which do not differ substantially in terms of their attenuation properties from the surrounding soft tissue, cannot be examined in a conventional fashion as a result of the lack of contrast.

However, it is precisely such examinations that have become very important in diagnostic medicine. Angiographic examinations are, in the meantime, used to diagnose a number of different vessel disorders. Thus, for example, angiographic examinations can be used to diagnose arterial disorders such as e.g. arteriosclerosis and vessel narrowing connected therewith, sacculation and impending vascular occlusion, and also venous disorders, such as e.g. thromboses.

In radiology, C-arm systems have up until now been predominantly used for angiographic examinations. The flat-panel detectors available in these systems can generate projection images with high spatial resolution and high coverage of the examination region. As a result of the small differences in the attenuation properties between the vessels and the surrounding soft tissue with respect to X-ray radiation, angiographic examinations are carried out using a contrast agent in order to increase the image contrast. Vessel structures and organs connected thereto are made visible by indirect means in the projection image as a result of the volume taken up by the contrast agent. Depending on the medical question, it may be desirable in the process to generate a projection image which merely contains the contrast agent. That is to say image structures of bone and soft tissue should be suppressed in this case.

A conventional technique for masking such image structures is provided by digital subtraction angiography. In the process, a native projection image of the examination region without contrast agent is firstly recorded from a previously set projection direction by means of a C-arm system. In a second step, a series of projection images are acquired from the same projection direction after the contrast agent was injected. The previously acquired native projection image is subsequently subtracted from these projection images, and so only differences between the data become visible. Thus, ideally, it is merely the contrast-agent filled vessel and organs that can be seen in the resulting projection image while the bones and the soft tissue are eliminated from the image.

A significant disadvantage of this method emerges from the fact that the projection images used for the subtraction were recorded at different times. A patient movement that took place between the recording times, as already caused by breathing, must be compensated for by registering the two projection images before the actual subtraction. Sufficiently good results can in general only be achieved in the process if the registration is carried out on the basis of computationally expensive affine image transformations.

However, despite image registration, many situations do not allow mathematically completely accurate estimates of the patient movement, which leads to the formation of a certain amount of shadowing in the region of erroneously registered image structures in the resulting projection image.

These days, computed tomography systems are also used for examining vessels. The so-called CT angiography, also abbreviated as CTA, is based on a 3D image reconstruction, in which projections are acquired from a multiplicity of different projection directions during a rotation of the recording system around the patient and combined with each other to form a slice image. The vessels to be illustrated in the slice image are subsequently segmented from the slice images using image-processing algorithms and output in freely rotatable 3D representations. Even without generating a native slice image, the CTA examinations are disadvantageous in that the patient is exposed to an increased X-ray dose compared to an angiographic examination using a C-arm system as a result of the multiplicity of projections from different angular directions required for the image reconstruction.

SUMMARY

At least one embodiment of the present invention specifies a method and/or a computed tomography scanner by which a medical field of application of the computed tomography scanner is extended.

A method is disclosed for carrying out an angiographic examination of a patient using a computed tomography scanner, and a computed tomography scanner as per the coordinate is also disclosed.

The inventors have discovered that the application of computed tomography scanners can be extended to fields of application that were previously the reserve of other modalities, in particular C-arm systems with flat-panel detectors. The field of application can be extended particularly easily for such computed tomography scanners in which the recording system is configured to have a multi-row detector and small pixel sizes such that each individual projection obtains large z-coverage with, at the same time, high spatial resolution. Thus, it was recognized that a computed tomography scanner can be used to carry out an angiographic examination that delivers a result comparable to a subtraction angiography with a C-arm system.

Here, the method according to at least one embodiment of the invention for carrying out an angiographic examination of a patient using a computed tomography scanner with at least one recording system mounted on a gantry such that it can rotate about a z-axis comprises:

a) acquiring projection data from at least one prescribed angular position of the gantry for at least two different energies of X-ray radiation, and b) combining the projection data corresponding to the respective angular position to form a resulting projection image, in which at least one substance, which should be displayed selectively, is imaged with a high image contrast compared to the respective individual projection data.

Here, the projection data can be acquired in different fashions. According to one advantageous embodiment of the invention, the projection data is obtained with a non-rotating gantry after setting the gantry to the prescribed angular position. In a further advantageous variant of at least one embodiment of the invention, the projection data is obtained with a rotating gantry such that acquisition of projection data only takes place when the gantry passes through the at least one prescribed angular position.

In other words, this means that the acquisition of the projection data is implemented by pulsed generation of the X-ray radiation at the at least one prescribed angular position. Moreover, the projection data is preferably recorded from a plurality of prescribed angular positions. In this case, a plurality of resulting projection images are calculated, with each projection image showing the substance, which should be displayed selectively, from a specific angular position set in advance. The prescribed angular position of the gantry is a fixed angular position, although it may vary slightly for scanning reasons or as a result of positioning tolerances.

Here, the combination takes place taking into account a functional relationship that is specific to the substance between utilized X-ray radiation energy and an observed attenuation property of the X-ray radiation passing through the substance.

The projection data supplies two attenuation values with different X-ray energies for each pixel of the resulting projection image. By evaluating the value combinations taking into account the attenuation properties, which are specific to the selected substance and depend on the energy, it is possible to display those image regions with an improved signal-to-noise ratio or an improved image contrast that contain the substance. In the case of angiographic examinations, the selected substance preferably is the contrast agent. However, depending on the medical question, it may also be required to blend other or further substances into the projection image. Thus, in order to evaluate e.g. morphological information, it may be necessary alternately to display the contrast agent in the projection image with and without soft tissue or with and without bone. In these cases, a plurality of substance-specific criteria are applied to the two projection data records.

However, the method according to at least one embodiment of the invention is also connected with the further advantages set out below. The utilized multispectral technique avoids a complicated and error-prone registration of various projection data records recorded over relatively long time intervals. This is because, depending on the type and configuration of the detector, the projection data is acquired simultaneously or successively over very short time intervals of the order of a few microseconds, and so no patient movements of note can be observed in successive projection data. The use of a multispectral technique moreover also dispenses with the acquisition of a native projection image of the examination region without contrast agent. This simplifies the workflow of the examination to be carried out.

Within the scope of an intervention, it may be necessary during the intervention to interrupt the projection-based angiographic imaging from a fixed angular position without gantry rotation in order to generate a 3D control image. The method according to at least one embodiment of the invention is particularly advantageous in that the use of a computed tomography scanner allows, without delay or change in modality, a switch between the operating modes for projection-based angiography and the operating mode for generating a 3D image whilst rotating the gantry.

The projection data is acquired by different X-ray spectra in an advantageous embodiment of the invention. Here, the X-ray spectra are preferably generated by changing an X-ray tube voltage or a radiation filter. This allows a rapid change in the X-ray spectra of the order of microseconds, and so successive projection data can be acquired over short time intervals and hence with little patient movement.

The acquisition of the projection data by an energy-selective X-ray detector, more particularly by a direct conversion semiconductor detector or an optically counting detector, is particularly advantageous. In this case, the two projection data records are acquired at the same time. As a result of this, a patient movement need not be taken into account when combining the projection data. Moreover, by acquiring both records of projection data relating to the different energies of the X-ray radiation at the same time, merely a single recording is required, and so the X-ray dose applied to the patient is reduced compared to the above-described methods.

A higher spatial resolution in the resulting projection image compared to the detector can moreover advantageously be obtained if projection data is acquired at different sub-pixel positions at the same X-ray radiation energy and combined. This works in particular by evaluating the gradual profile of the attenuation values from mutually corresponding pixels when additionally taking into account the imaging function specific to the detector. This scanning method makes it possible to achieve spatial resolutions in the sub-millimeter range, which are comparable to the resolution of flat-panel detectors in C-arm systems.

In a further advantageous embodiment of the invention, the projection data is acquired within a certain z-axis section. A relative repositioning between measurement region and examination region can be implemented in a different fashion. A simple option includes carrying out a continuous or oscillatory motion of a patient table, which serves to support the patient, in the direction of the z-axis. However, it would likewise be feasible to implement the repositioning by means of a flying focus. An oscillatory motion of the focus of an X-ray source can in particular implement very rapid repositionings because the focus can be set to different positions without any inertia of note. As a result, it is possible to generate projection images that, compared to the individual projection, have an extended field of view in the longitudinal direction of the patient. In other words, this means that, compared to the detector, the resulting projection image has a larger z-coverage, which is particularly advantageous when using detectors with a small number of rows.

Projection data acquisition along the z-section is preferably carried out on opposite sides for the different X-ray spectra, with or without overlap of the scan regions. As a result of the known displacements of the patient table, projection data can be merged in a simple fashion before being combined.

In an example embodiment of the invention, a concentration of the substance is established from the projection data for each pixel of the projection image using a two or three material decomposition, as also disclosed in, for example, DE 10 2007 024 158 A1, the entire contents of which are hereby incorporated herein by reference.

The projection image can likewise advantageously be established using few computational resources from a weighted subtraction of the projection data with substance-specific weightings.

A tissue or vessel structure to be displayed has particularly few overlays in the projection image if the angular position to be set is selected automatically, depending on a predetermined examination region of the patient and taking into account previous anatomical knowledge. This can ensure optimized imaging in respect of the morphological information.

A second aspect of at least one embodiment of the invention relates to a computed tomography scanner with at least one setting device, acquisition device, and combination device, which are configured as per the above-described method.

BRIEF DESCRIPTION OF THE DRAWINGS

In the following text, the invention will be explained in more detail on the basis of exemplary embodiments and on the basis of drawings, in which:

FIG. 2 shows a block-diagram-like display of the method according to an embodiment of the invention, and FIG. 3 shows a scanning scheme when continuously repositioning the patient support device in the z-direction.

DETAILED DESCRIPTION OF THE EXAMPLE EMBODIMENTS

Figure 1:
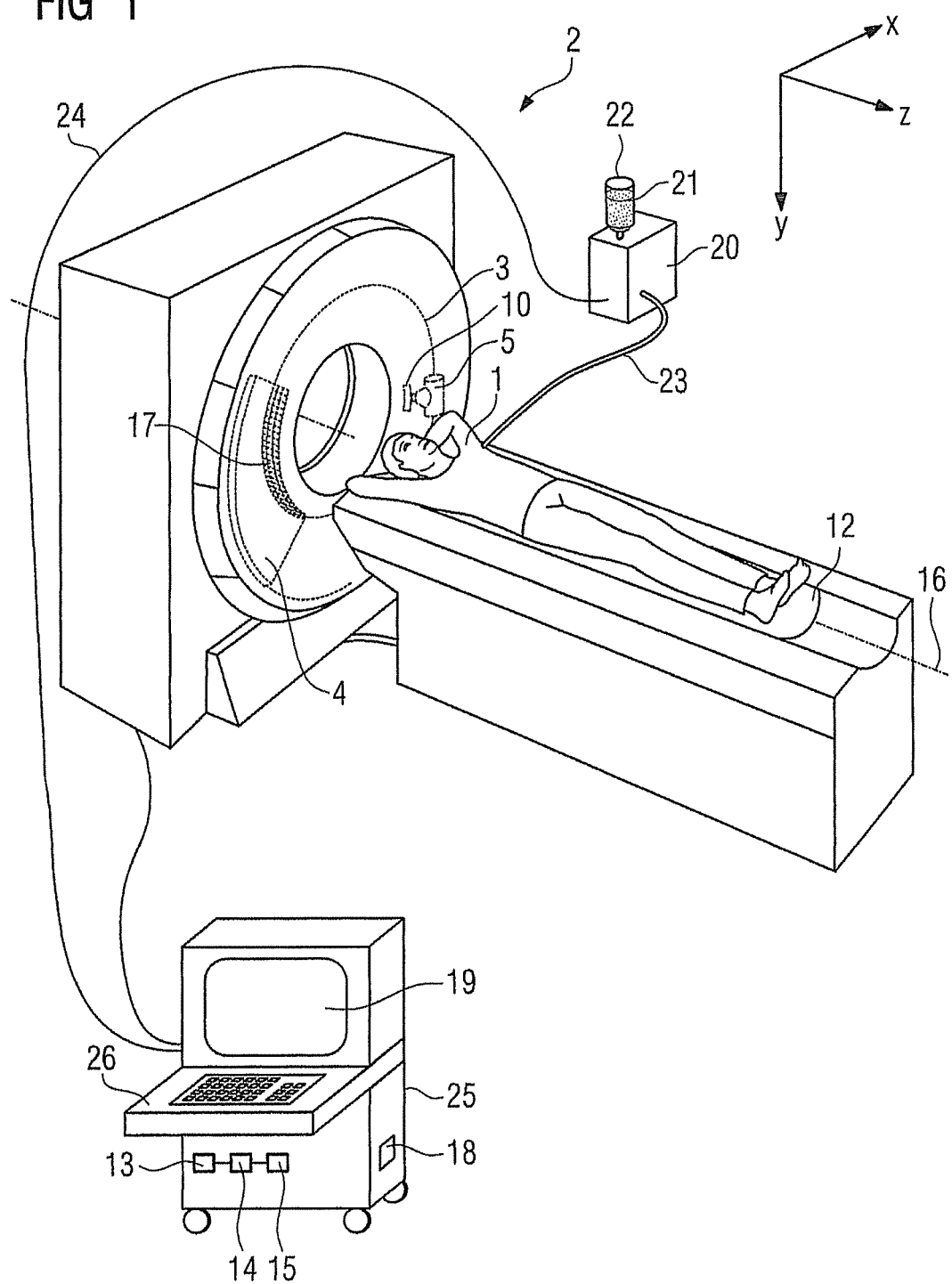
FIG. 1 shows a computed tomography system for carrying out the method according to an embodiment of the invention, partly in a perspective view and partly like a block diagram.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there , are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In the figures, equivalent or functionally equivalent elements are denoted by the same reference sign. If elements are repeated in a figure, only one element has in each case been provided with a reference sign for reasons of clarity. The illustrations in the figures are schematic and not necessarily to scale, wherein scales may vary between the figures.

FIG. 1 shows a computed tomography scanner 2, which is suitable for carrying out the method according to an embodiment of the invention for the projection-based angiographic examination or which is suitably equipped. It comprises a patient table 12 for supporting a patient 1 to be examined, which patient table can be repositioned along a system axis 16. In the following text, the system axis 16 is also referred to as z-axis, which can be repositioned in the measurement field with the patient 1. It furthermore comprises a gantry 3 (not illustrated) with a recording system 4, 5 that is mounted such that it can rotate about a system axis 16. The recording system 4, 5 has an X-ray tube 5 and a detector 4, which are aligned opposite to one another such that, during operation, X-ray radiation emerging from the focus of the X-ray tube 5 impinges on the detector 4. The detector 4 is structured in individual pixels 17 for spatially resolved acquisition of the X-ray radiation, which pixels are arranged in a number of detector rows. Currently, use is already made of detectors 4 that have a total of 64 or more rows and have a spatial resolution in the sub-millimeter range. The detector 4 generates a record of projection data for each projection. Here the projection data represents the attenuation values of all pixels 17 of X-ray radiation attenuated by the patient 1. It is transmitted to an image reconstruction unit 18 and combined to form a resulting image, which can be displayed on a display unit 19.

It is well-known that such a computed tomography scanner 2 is used for 3D image reconstruction. In order to record an image of an examination region, projection data is acquired from a multiplicity of different projection directions while the recording system 4, 5 rotates. In the case of a helical scan, there is, for example, continuous repositioning of the patient table 12 in the direction of the system axis 16 at the same time as a rotation of the recording system 4, 5. The X-ray tube 5 and the detector 4 hence move in a helical path around the patient 1 in this type of scan.

Furthermore, a contrast-agent instrument 20 is connected to the computed tomography scanner 2 and the former is used to inject contrast agent 21 into the bloodstream of the patient 1 during an examination such that the contrast-agent-filled vessels and the organs of the patient 1 penetrated by contrast agent 21 can be identified in the image. An amount of contrast agent 21 that can be set is pumped at a flow speed that can be set and in a time controlled automated fashion from a storage container 22 and into a vein of the patient 1 via a contrast-agent tube 23. The parameters required for this are stored in application-specific contrast-agent protocols. They can be called or actuated via an electrical connection 24 between the computational unit 25 and the contrast-agent instrument 20.

Subtraction angiographies for examining vessels using a contrast agent 21 were, up until now, carried out by C-arm systems. The trend in modern computed tomography scanners is toward increasing numbers of detector rows to obtain high z-coverage with, at the same time, increased spatial resolution. Triggered by this trend, the inventors have realized that examinations can be carried out by such a computed tomography scanner 2, which methods provide a result that is comparable to subtraction angiography and moreover have additional advantages.

FIG. 2 shows a procedure according to an embodiment of the inventive method for carrying out a projection-based angiographic examination using the computed tomography scanner 2.

In a first step 6, the gantry 3 is firstly set to a fixed angular position in this example embodiment. The angular position is prescribed either by the user via an input interface 26 or in an automated fashion whilst evaluating an anatomical model of the examination region or a 3D control image generated before the start of the examination.

In a subsequent second step 7, projection data L1, L2, H1, H2 is acquired from this angular position at different X-ray radiation energies after the contrast agent was injected, without the gantry 3 rotating. This is achieved by a periodic change in the X-ray spectrum for successive projections L1, H1, L2, H2, for example by periodic switching of the X-ray tube voltage between 80 kV and 120 kV or a periodic change in the pre-filtering. If an energy-selective detector 4 is used, the acquisition of projection data L1, L2, H1, H2 at different energies is even possible whilst maintaining the X-ray spectrum with a single recording. By way of example, optical counting detectors on the basis of SIPM technology or semiconductor-based direct conversion detectors on the basis of a CdTe-compound can be used as energy selective detectors 4.

In a third step 8, the projection data L1, L2, H1, H2 is combined to form a resulting projection image 9, in which the contrast agent 21 is imaged with a high contrast compared to the individual projection data L1, L2, H1, H2. This is achieved by using a weighted subtraction of the high-energy projection data H1, H2 from the low-energy projection data L1, L2. However, it is also possible to determine a contrast agent 21 concentration by way of a known two or three component decomposition or other dual-energy methods known for this purpose.

In order to increase the contrast in the resulting image, it is also possible to acquire and combine projection data L1, L2, H1, H2 from more than only two different energies. Depending on the medical question, it goes without saying that other substances can also be displayed, either on their own or selectively in combination, instead of the contrast agent 21 by appropriate combination of the projection data.

In order to increase the measurement region, the projection data L1, L2, H1 H2 is acquired along the z-axis in this example embodiment by relative repositioning of the patient 1 in relation to the recording system 4, 5. In this respect there is, in the simplest case, a continuous repositioning of the patient table 12 in the direction of the patient longitudinal axis. A scanning scheme for such a scan is shown in FIG. 3. The projection data L1, L2, H1, H2 is acquired within a z-axis section 11. In the process, low-energy projection data L1, L2 and high-energy projection data H1, H2 are acquired on opposite sides. The successive projection data at the same energy L1, L2 and H1, H2 have a small overlap in this case. The patient table 12 can be repositioned at such a great speed that patient movements in acquired projection data L1, L2, H1, H2 are small despite the time offset and do not have to be taken into account during the combination. The merging of the projection data L1 and L2 or H1 and H2 at the same energy is simple because the pixel offset of the projection data L1, L2, H1, H2 with respect to one another can be determined directly from the known speeds of the patient table 12 during the repositioning. Moreover, perfusion measurements for acquiring a time profile of a contrast-agent concentration can be implemented by a periodic to-and-fro motion of the patient table 12. The projection data L1, L2, H1, H2 acquired thus is combined to form the resulting projection image 9. In the projection image 9, it is merely the substances that should be imaged selectively that are visible, in this case only the contrast agent 21. Bones 27, which can be seen in the individual projection data L1, L2, H1, H2, are eliminated in the projection image 9.

Instead of the repositioning of the patient table 12 described here, or in combination with this, it is also possible to reposition the X-ray tube 5 focus. In a simplest case, moreover, it is only two recordings or two projection data records that are acquired at different energies of the X-ray radiation without additional relative repositioning between measurement region and examination region. Moreover, the projection data can also be acquired during rotational operation of the gantry by pulsed generation of the X-ray radiation from the fixedly defined angular position. Moreover, depending on the medical question, it may be necessary for a projection image to be required for different angular positions of the gantry. In this case, the projection data will be acquired from a multiplicity of prescribed angular positions of the gantry, wherein the projection data corresponding to the respective angular position is in each case combined to form a resulting projection image.

In summary, the following statements can be made:

An embodiment of the invention relates to a method and a computed tomography scanner 2 for carrying out an angiographic examination of a patient 1, wherein the utilized computed tomography scanner 2 has at least one recording system 4, 5 mounted on a gantry 3 such that it can rotate about a z-axis. Projection data L1, L2, H1, H2 is acquired from at least one prescribed angular position of the gantry for at least two different energies of X-ray radiation. The projection data L1, L2, H1, H2 is subsequently combined to form a resultant projection image 9 by evaluating the projection data L1, L2, H1, H2 corresponding to the respective angular position, in which projection image at least one substance 21, which should be displayed selectively, is imaged with a high image contrast compared to the respective individual projection data L1, L2, H1, H2. This procedure extends the field of application of the computed tomography scanner 2 to projection-based angiography examinations, which were previously restricted to C-arm systems. 3D image reconstruction methods and projection methods can be carried out on opposite sides and with great flexibility during an examination, without the need for an additional modality. By using a multispectral technique, it is possible to dispense with recording a native projection data record without contrast agent 21. The projection data L1, L2, H1, H2 at the different energies are moreover acquired with no or little time offset, and so a computationally expensive and error-prone registration of the data records can be dispensed with.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method involving angiographic examination of a patient using a computed tomography scanner with at least one recording system mounted on a gantry so as to be rotatable about a z-axis, the method comprising:
   acquiring projection data from a single angular position of the gantry with respect to the patient for at least two different energies of X-ray radiation, the gantry being stationary with respect to the single angular position while acquiring the projection data; and
   combining the acquired projection data from the single angular position to form a resulting projection image, in which at least one substance, which is selectively displayable, is imaged with a relatively high image contrast compared to the respective individual projection data.

2. The method as claimed in claim 1, wherein the projection data is obtained with the gantry such that the acquisition of projection data only takes place when the gantry is aligned with the single angular position.

3. The method as claimed in claim 2, wherein projection data is recorded at the single angular position.

4. The method as claimed in claim 1, wherein the projection data is acquired by different X-ray spectra.

5. The method as claimed in claim 4, wherein the different X-ray spectra are generated by changing an X-ray tube voltage or a radiation filter.

6. The method as claimed in claim 1, wherein the projection data is obtained by an energy-selective X-ray detector.

7. The method as claimed in claim 6, wherein the projection data is obtained by a direct conversion semiconductor detector.

8. The method as claimed in claim 1, wherein the projection data is acquired at different sub-pixel positions at the same X-ray radiation energy.

9. The method as claimed in claim 8, wherein there is a continuous or oscillatory motion of a patient table, serving to support the patient, in the direction of the z-axis.

10. The method as claimed in claim 8, wherein the focus of an X-ray source is made to undergo an oscillatory motion.

11. The method as claimed in claim 1, wherein the projection data is acquired within one z-axis section.

12. The method as claimed in claim 11, wherein there is a continuous or oscillatory motion of a patient table, serving to support the patient, in the direction of the z-axis.

13. The method as claimed in claim 11, wherein the focus of an X-ray source is made to undergo an oscillatory motion.

14. The method as claimed in claim 1, wherein a concentration of the at least one substance is established from the projection data for each pixel of the projection image using a two or three material decomposition.

15. The method as claimed in claim 1, wherein the projection image is established from a weighted subtraction of the projection data with substance-specific weightings.

16. The method as claimed in claim 1, wherein the single angular position to be set is selected automatically, depending on an examination region of the patient and taking into account previous anatomical knowledge, such that a tissue or vessel structure to be illustrated has as few overlays as possible.

17. The method as claimed in claim 1, wherein the combining combines the acquired projection data from the single angular position without performing a registration procedure between the projection data acquired at the at least two different energies.

18. The method as claimed in claim 1, wherein the acquiring acquires the projection data at mutually different X-ray spectra to generate the projection data along the z-axis.

19. A computed tomography scanner with at least one recording system mounted on a gantry so as to be rotatable about a z-axis, embodied to carry out an angiographic examination of a patient and comprising:
   acquisition means for acquiring projection data from a single angular position of the gantry with respect to the patient for at least two different energies of X-ray radiation, the gantry being stationary with respect to the single angular position while acquiring the projection data; and
   combination means for combining the acquired projection data from the single angular position to form a resulting projection image, in which at least one substance, which is selectively displayable, is imaged with a relatively high image contrast compared to the respective individual projection data.

20. The computed tomography scanner of claim 19, wherein the combination means is configured to combine the acquired projection data from the single angular position without performing a registration procedure between the projection data acquired at the least two different energies.

21. The computed tomography scanner of claim 19, wherein the acquisition means is configured to acquire the projection data at mutually different X-ray spectra to generate the projection data along the z-axis.

22. A computed tomography scanner with at least one recording system mounted on a gantry so as to be rotatable about a z-axis, embodied to carry out an angiographic examination of a patient and comprising:
   an acquisition device to acquire projection data from a single angular position of the gantry with respect to the patient for at least two different energies of X-ray radiation, the gantry being stationary with respect to the single angular position while acquiring the projection data; and
   a combination device to combine the acquired projection data from the single angular position to form a resulting projection image, in which at least one substance, which is selectively displayable, is imaged with a relatively high image contrast compared to the respective individual projection data.

23. The computed tomography scanner of claim 22, wherein the combination device is configured to combine the acquired projection data from the single angular position without performing a registration procedure between the projection data acquired at the least two different energies.

24. The computed tomography scanner of claim 22, wherein the acquisition device is configured to acquire the projection data at mutually different X-ray spectra to generate the projection data along the z-axis.

25. A tangible computer readable medium including program segments for, when executed on a computer device, causing the computer device to implement the method of claim 1.

* * * * *